United States Patent [19]
Fukuma et al.

[11] Patent Number: 5,886,780
[45] Date of Patent: Mar. 23, 1999

[54] REFRACTOMETER WITH DEFLECTING ELEMENT

[75] Inventors: Yasufumi Fukuma; Takefumi Hayashi; Kazuhiko Tamura, all of Tokyo, Japan

[73] Assignee: Kabushiki Kaisha Topcon, Tokyo, Japan

[21] Appl. No.: 887,264

[22] Filed: Jul. 2, 1997

[30] Foreign Application Priority Data

Jul. 3, 1996 [JP] Japan ................................ 8-172716
Jul. 3, 1996 [JP] Japan ................................ 8-172717

[51] Int. Cl.$^6$ ........................... G01N 21/41; G02C 1/04
[52] U.S. Cl. ........................................ 356/128; 351/205
[58] Field of Search ........................ 356/124, 128; 351/205–211

[56] References Cited

U.S. PATENT DOCUMENTS

4,544,248 10/1985 Nunokawa ........................... 351/206
4,761,070 8/1988 Fukuma ............................... 351/205

*Primary Examiner*—Robert Kim
*Assistant Examiner*—Amanda Merlino
*Attorney, Agent, or Firm*—Finnegan, Henderson, Farabow, Garrett & Dunner, L.L.P.

[57] ABSTRACT

A refractometer comprising an optical pattern-beam projection system for projecting a pattern,light beam onto the fundus of a tested eye to measure refractive power of the tested eye, and an optical light-receiving system for receiving the pattern light beam reflected at the fundus to compute the refractive power of the tested eye. A deflecting member is inserted into an optical path of the optical pattern-beam projection system for deflecting the pattern light beam with respect to an optical axis of the optical pattern-beam projection system and then projecting the deflected pattern light beam onto the fundus.

8 Claims, 8 Drawing Sheets

REFRACTOMETER WITH DEFLECTING ELEMENT

BACKGROUND OF THE INVENTION

1. Field of the Invention

The present invention relates to a refractometer that is equipped with an optical pattern-beam projection system which projects a pattern light beam onto the fundus of a subject's eye to measure the refractive power of the eye and an optical light-receiving system which receives the pattern light beam reflected at the fundus and computes the refractive power of the eye.

2. Description of the Related Art

In a conventional refractometer, a ring-shaped pattern light beam for measuring the refractive power of a tested eye is projected by an optical pattern-beam projection system. The ring-shaped pattern light beam is reflected at the fundus and received as a pattern image with a light receiving element. In this way, the refractive power of the tested eye is measured.

Figure 9:
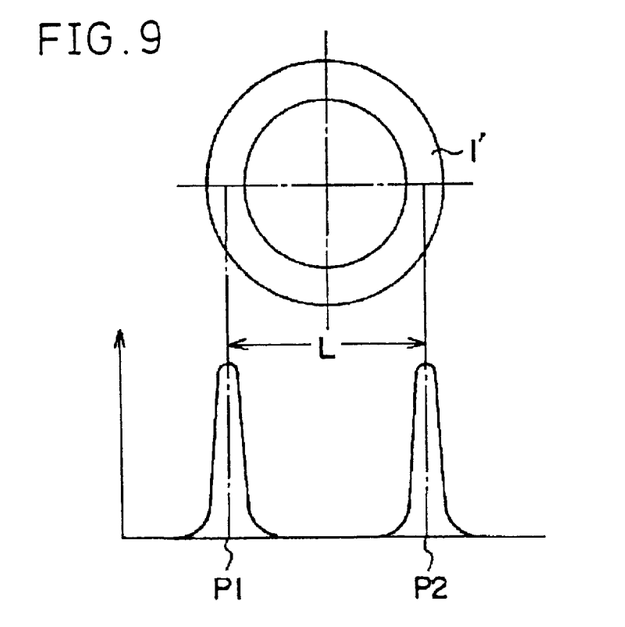
FIG. 9 is a schematic view showing the relationship between a pattern image projected on a light receiving element by a conventional refractometer and a peak position.

In a refractometer such as this, when a tested eye has normal vision (±0 diopter), a pattern image 1' with a ring shape and a predetermined size is projected on a light receiving element, as shown in FIG. 9. When a tested eye has farsightedness, the pattern image is larger than that in normal vision. Also, when a tested eye has nearsightedness, the pattern image is smaller than that in normal vision.

The center positions P1 and P2 of the width of the pattern image 1' projected on the light receiving element are detected by the peak positions of a light quantity distribution. Based on the detected peak positions P1 and P2, the inter center distance L of the pattern image 1' (i.e., distance between P1 and P2) is computed to obtain the refractive power of a tested eye.

Figure 10:
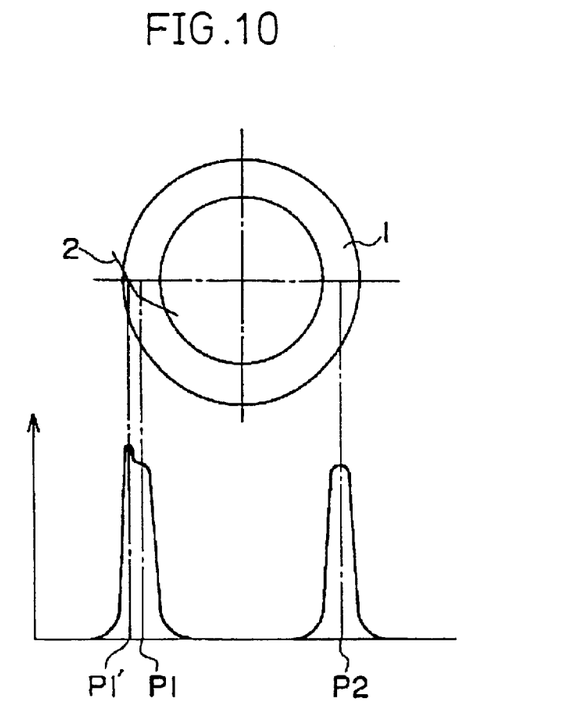
FIG. 10 is a schematic view showing the relationship between a pattern image projected on a light receiving element by the conventional refractometer and a peak position, a scar having existed on the pattern image.

However, in the conventional refractometer, for example, when a vein or scar 2 exists at the measured position of the inter center distance on the pattern light beam 1 projected on the fundus of a tested eye, as shown in FIG. 10, a portion corresponding to the scar 2 is obtained as a peak position, and a center position P1' shifted from an actual center position P1 is detected. For this reason, there arises the problem that normal vision is measured as astigmatism by mistake.

SUMMARY OF THE INVENTION

Accordingly, it is an object of the present invention to provide a refractometer which is capable of preventing a mistaken measurement which results from veins or scars on the fundus of a tested eye.

To achieve the object of the present invention, a refractometer according to an aspect of the present invention comprises an optical pattern-beam projection system for projecting a pattern light beam onto the fundus of a tested eye to measure refractive power of the tested eye, an optical light-receiving system for receiving the pattern light beam reflected at the fundus to compute the refractive power of the tested eye, and a deflecting member inserted in an optical path of the optical pattern-beam projection system for deflecting the pattern light beam with respect to an optical axis of the optical pattern-beam projection system and then projecting the deflected pattern light beam onto the fundus.

In a preferred form of the present invention, the optical pattern-beam projection system and the optical light-receiving system share a portion of an optical system, and the deflecting member is inserted into the shared portion.

In another preferred form of the present invention, the refractometer further comprises a driving means for rotating the deflecting member about the optical axis of the optical pattern-beam projection system.

In still another preferred form of the present invention, the refractometer further comprises an optical illumination system for illuminating the fundus, an optical observation system for observing an image on the fundus illuminated by the optical illumination system, and set means for setting a drive quantity which is driven by drive means.

In still another preferred form of the present invention, the refractometer further comprises a position detection means for detecting a position of the deflecting member, a computation means for computing a position on the fundus of the tested eye where the pattern light beam is projected, based on the result of the detection of the position detection means, and a display means for synthesizing and displaying the image on the fundus and the pattern image, based on the result of the computation of the computation means.

A refractometer according to another aspect of the present invention comprises an optical pattern-beam projection system for projecting a pattern light beam onto the fundus of a tested eye to measure refractive power of the tested eye, and an optical light-receiving system for receiving the pattern light beam reflected at the fundus to compute the refractive power of the tested eye. The refractometer further comprises a first deflecting member provided in an optical path of the optical pattern-beam projection system for deflecting the pattern light beam with respect to an optical axis of the optical pattern-beam projection system and then projecting the deflected pattern light beam onto the fundus, and a second deflecting member provided in an optical path of the optical light-receiving system for deflecting the pattern light beam reflected at the fundus toward an optical axis of the optical light-receiving system.

In a preferred form of the present invention, the deflecting members are inserted at positions which are approximately conjugate with the pupil of the tested eye.

In another preferred form of the present invention, the deflecting members are rotatable about the optical axes in synchronization.

BRIEF DESCRIPTION OF THE DRAWINGS

The present invention will be described in further detail with reference to the accompanying drawings wherein.

BEST MODE FOR CARRYING OUT THE INVENTION

First Embodiment

Figure 1:
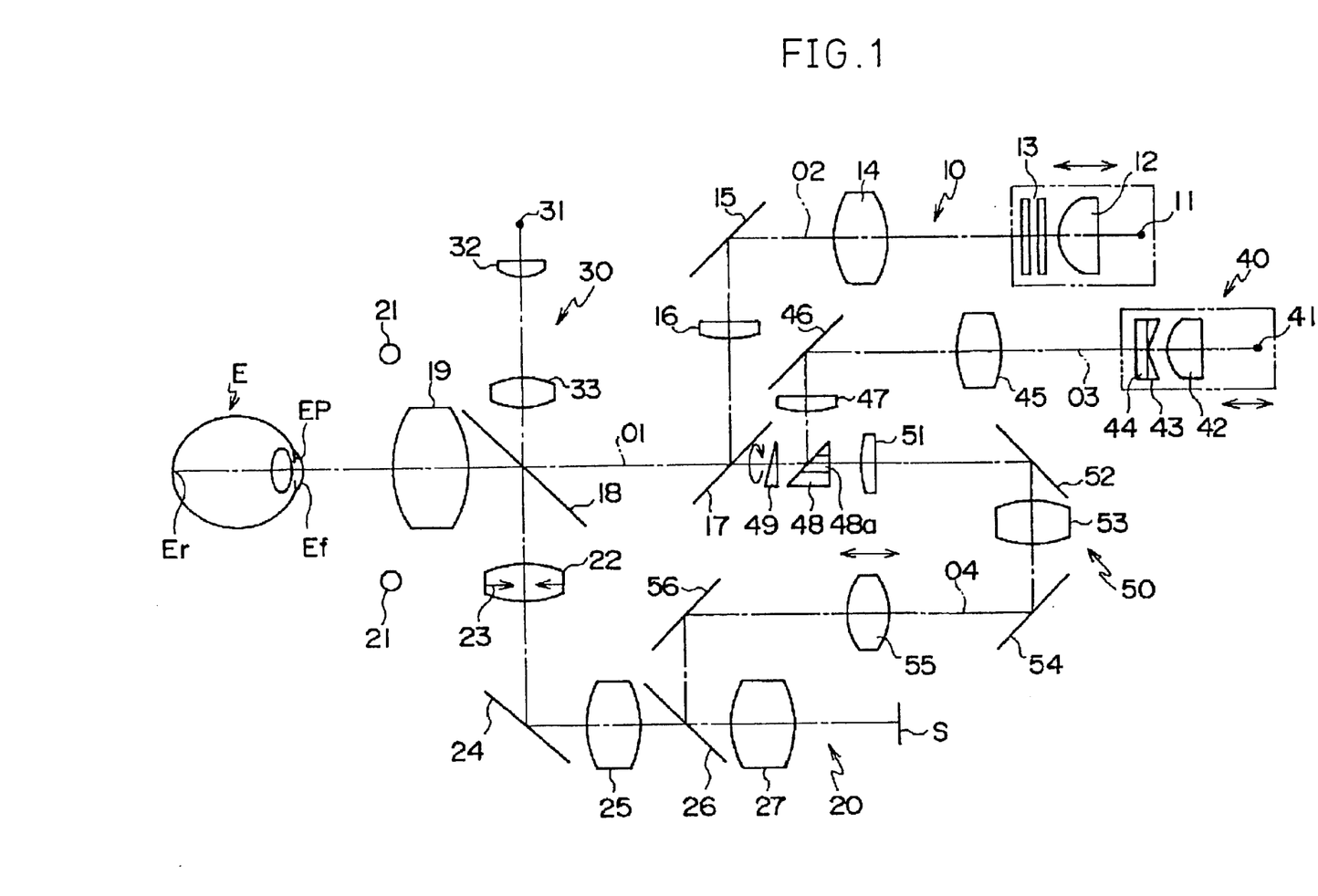
FIG. 1 is a schematic view showing a refractometer according to a first embodiment of the present invention.

Referring to FIG. 1, there is shown an optical system which is applied to a refractometer of the present invention. In the figure, reference numeral 10 denotes an optical target projection system which projects a target onto a fundus Er to fix a tested eye on the target with and without accommodation E. Reference numeral 20 denotes an optical observation system which observes the front eye portion Ef of the tested eye E, and reference numeral 30 denotes an optical scale projection system which projects a diopter scale onto a light receiving element S. Reference numeral 40 denotes an optical pattern-beam projection system which projects a pattern beam onto the fundus Er to measure the refractive power of the tested eye E, and reference numeral 50 denotes an optical light-receiving system which receives on the light receiving element S a light beam reflected from the fundus Er.

The optical target projection system 10 is equipped with a light source 11, a collimator lens 12, a target plate 13, a relay lens 14, a mirror 15, a relay lens 16, a dichroic mirror 17, a dichroic mirror 18, and an objective lens 19.

Visible light emitted from the light source 11 is collimated by the collimator lens 12 and then is transmitted through the target plate 13. The target plate 13 is provided with a target for collimating and fogging the tested eye E. The target light beam is transmitted through the relay lens 14 and reflected by the mirror 15. The reflected light beam is reflected by the dichroic mirror 17 via the relay lens 16 and is guided to the principal axis O1 of the main body of the apparatus. Next, the target light beam is transmitted through the dichroic mirror 18 and then is guided to the test eye E via the objective lens 19.

The light source 11, the collimator lens 12, and the target plate 13 are formed as a unit so that they can move along the optical axis O2 of the optical target projection system 10, in order to collimate and fog the tested eye E.

The optical observation system 20 has a light source 21, the aforementioned objective lens 19, the aforementioned dichroic mirror 18, a relay lens 22, a diaphragm 23, a mirror 24, a relay lens 25, a dichroic mirror 26, an imaging lens 27, and a light receiving element S.

A light beam emitted from the light source 11 directly illuminates the front eye portion Ef of the tested eye E. The light beam reflected by the front eye portion Ef is reflected by the dichroic mirror 18 via the objective lens 19. The reflected light beam is transmitted through the relay lens 22 and, at the same time, is caused to pass through the diaphragm 23. The reflected light beam is reflected by the mirror 24 and then is transmitted through the relay lens 25 and the dichroic mirror 26. The light beam from the dichroic mirror 26 is projected on the light receiving element S by the imaging lens 27.

The optical scale projection system 30 is constituted by a light source 31, a collimator lens 32 with a diopter scale, a relay lens 33, the aforementioned dichroic mirror 18, the aforementioned relay lens 22, the aforementioned diaphragm 23, the aforementioned mirror 24, the aforementioned relay lens 25, the aforementioned dichroic mirror 26, the aforementioned imaging lens 27, and the aforementioned light receiving element S.

A light beam emitted from the light source 31 becomes a diopter scale light beam (a collimated light beam) when passing through the collimator lens 32. The collimated light beam is transmitted through the relay lens 33, the dichroic lens 18, the relay lens 22, and the diaphragm 23, and is reflected by the mirror 24. The light beam from the mirror 24 is transmitted through the dichroic mirror 26 and projected on the light receiving element S by the imaging lens 27.

The light receiving element S employs, for example, a two-dimensional area charged-coupled device (CCD). A monitor (not shown) displays the image of the front eye portion guided by the optical observation system 20 and also displays the image based on the diopter scale. An oculist performs vertical and horizontal alignment operations between the tested eye E and the main body of the apparatus so that the image of the front eye portion displayed on this monitor approaches the diopter scale image. Also, the oculist performs a longitudinal alignment operation. Note that when refractive power is measured after completion of the alignment operations, the light sources 21 and 31 are turned off, or a light beam to the light receiving element S is blocked by providing a shutter on the optical path leading from the dichroic mirror 18 to the dichroic mirror 26.

The optical pattern-beam projection system 40 is equipped with a light source 41, a collimator lens 42, a conical prism 43, a ring index plate 44, a relay lens 45, a mirror 46, a relay lens 47, a holed prism 48, an optical-axis deflection prism 49 as a deflecting member, the aforementioned dichroic mirror 17, the aforementioned dichroic mirror 18, and the aforementioned objective lens 19. The light source 41 and the ring index plate 44 are optically conjugate with each other, and the ring index plate 44 and the pupil Ep of the tested eye E are arranged at optical conjugate positions.

A light beam emitted from the light source 41 is collimated by the collimator lens 42 and is guided to the ring index plate 44 through the conical prism 43. The light beam emitted from the light source 41 is transmitted through a ring-shaped pattern portion formed on this ring index plate 44 and becomes a pattern light beam. The pattern light beam is transmitted through the relay lens 45 and then is reflected by the mirror 46. The pattern light beam reflected by the mirror 46 is transmitted through the relay lens 47 and reflected toward the principal axis O1 by the holed prism 48. The pattern light beam reflected by the holed prism 48 is transmitted through the dichroic mirrors 17 and 18 in the state where the pattern light beam is deflected obliquely with respect to the principal axis O1 by the optical-axis deflection prism 49. The obliquely deflected light beam from the dichroic mirror 18 is projected on the fundus Er by the objective lens 19.

Figure 2:
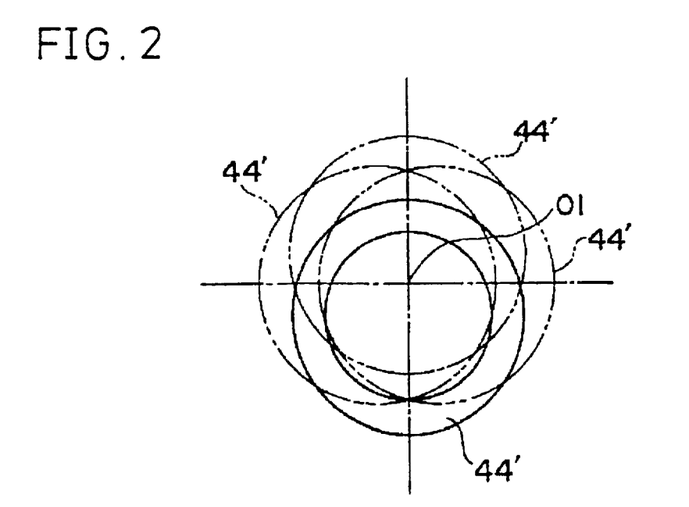
FIG. 2 is a plan view showing how pattern images are projected on the fundus of a tested eye.

The optical-axis deflection prism 49 is rotated on the principal axis O1 at high speed (see an arrow). The pattern light beam that is projected onto the fundus Er by this high-speed rotation goes around the principal axis O1 in the eccentric state, as shown in FIG. 2.

The optical light-receiving system 50 is constituted by the aforementioned objective lens 19, the aforementioned dichroic mirrors 18 and 17, an optical-axis deflection prism 49, the hole 48a of the aforementioned holed prism 48, a relay lens 51, a mirror 52, a relay lens 53, a mirror 54, a focusing lens 55, a mirror 56, the aforementioned dichroic mirror 26, the aforementioned imaging lens 27, and the aforementioned light receiving element S.

The focusing lens 55 is movable along the optical axes O3 and O4 of the optical systems 40 and 50 integrally with the light source 41, the collimator lens 42, and the conical prism 43, and the ring index plate 44.

The pattern light beam, guided to the fundus Er by the, optical pattern-beam projection system 40 and reflected at this fundus Er, is focused by the objective lens 19 and is guided to the optical-axis deflection prism 49 through the dichroic mirrors 18 and 17. By the principle of a backward movement of light, when the pattern light beam is transmitted through the optical-axis deflection prism 49, the same portion with respect to the principal axis O1 is guided to the hole 48a of the holed prism 48 and transmitted through this hole 48a.

The reflected pattern light beam passing through the hole 48a is transmitted through the relay lens 51 and reflected by the mirror 52. Thereafter, the reflected pattern light beam is transmitted through the relay lens 53 and guided to the mirror 54. The reflected pattern light beam from the mirror 54 is transmitted through the focusing lens 55 and reflected by the mirror 56 and the dichroic mirror 26. Thereafter, a pattern image is projected onto the light receiving element S by the image lens 27.

A description will now be given of the operation of the refractometer constructed as described above.

First, the light sources 11, 21, and 31 are lit to collimate the tested eye E, and also the alignment operation between the tested eye E and the main body of the apparatus is performed. At the time the alignment operation has been completed, the light sources 11, 21, and 31 are turned off and also the light source 41 is lit.

The illumination light beam emitted from the light source 41 is transmitted through the ring index plate 44 and becomes a ring-shaped pattern light beam. The ring-shaped pattern light beam is guided to the optical-axis deflection prism 49.

The optical-axis deflection prism 49 has been rotated on the optical axis O1 at high speed by a high-speed rotating apparatus (not shown), and therefore pattern images 44' are projected on the fundus Er in the state deflected from the optical axis O1 (see FIG. 2).

Figure 3:
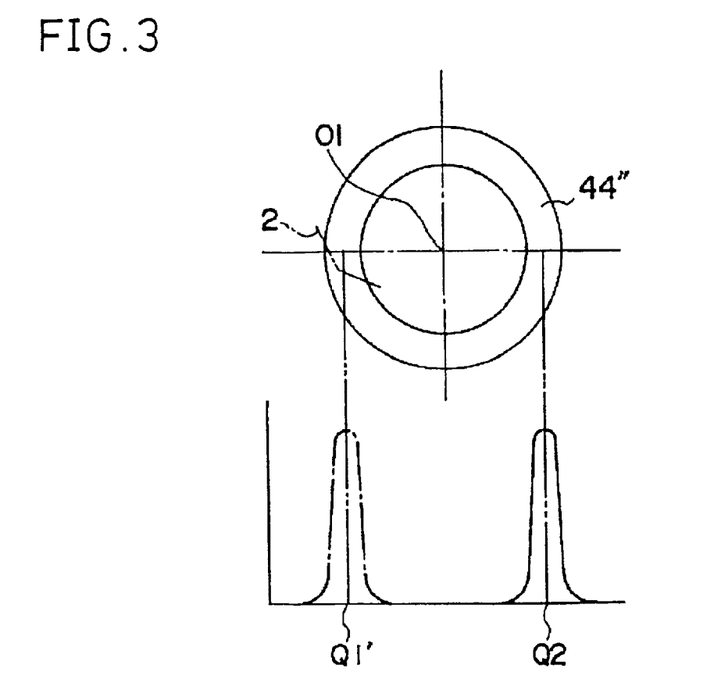
FIG. 3 is a schematic view showing the relationship between a pattern image projected on a light receiving element and a peak position.

The light beam reflected at the fundus Er is guided to the optical-axis deflection prism 49, and as shown in FIG. 3, the reflected light beam is projected on the light receiving element S as a pattern image 44" having the optical axis O1 as its center, in accordance with the principle of a backward movement of light.

The oculist stores a plurality of pattern images 44', projected on the light receiving element S based on the pattern image 44" projected at an arbitrary position of the positions projected on the fundus Er, on a storage medium such as a frame memory device.

For example, as shown in FIGS. 4(A) through (F), images corresponding to the pattern images 44' having a ring center O1' shifted from the optical axis O1 on the fundus Er are stored on a storage medium as pattern images 44" on the light receiving element S. In the states shown in FIGS. 4(A), (D), (E), and (F), the detected peak positions Q1 and Q2 has matched the center positions of the width of an actual image. However, in the states shown in FIGS. 4(B) and (C), the peak; positions Q3 and Q4 are at positions shifted from the center positions of the width of an actual image due to the influence of scar 2.

These peak positions Q1, Q2, and Q4 are averaged by the number of storages. With this, as shown in a graph of FIG. 3, the peak position Q1' close to the center position of the width of an actual image can be computed. By computing the distance between the centers of the width based on positional information about the peak position Q1 and the peak position Q2, the refractive power of an eye can be measured. Because the measuring method is well known in the prior art, a description thereof is omitted.

Figure 5A:
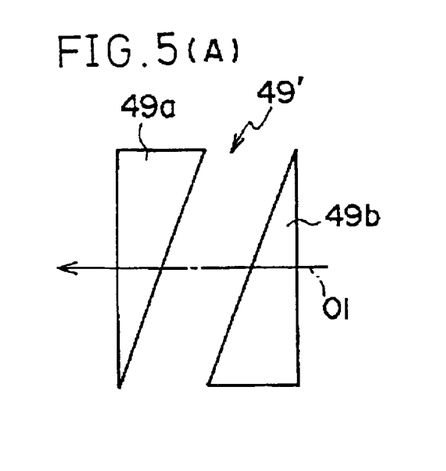
FIG. 5(A) is a schematic view of rotary prisms in the state where no light beam is deflected.
Figure 5B:
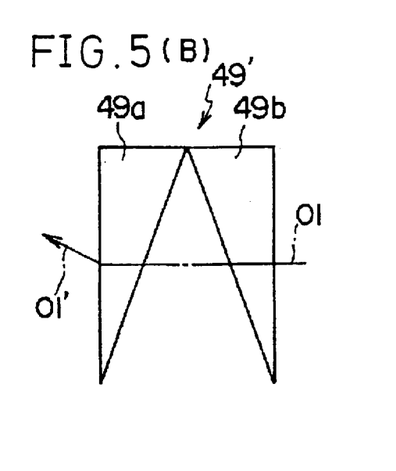
FIG. 5(B) is a schematic view of the rotary prisms in the state where a light beam is deflected.

In the aforementioned first embodiment, while the optical-axis deflection prism 49 has been employed as a deflecting member, a rotary prism 49' with two prisms 49a and 49b rotatable independently of and in synchronization with each other may also be employed as a deflecting member, as shown in FIG. 5(A). For example, as shown in FIG. 5(B), the entire rotary prism 49' may also be rotated on the optical axis O1 in the state where one prism 49b is rotated on the optical axis O1.

Since a shift in the emission angle with respect to the optical axis O1 can be adjusted and changed by rotating the prisms 49a and 49b independently of each other, an even wider adaptable range is obtainable compared with the case where the optical-axis deflection prism 49 is employed.

Figure 4A:
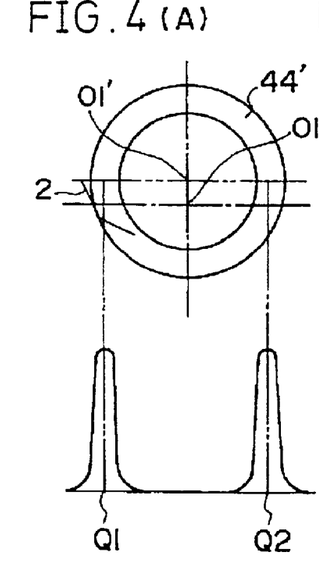
FIGS. 4(A) through (F) are schematic views showing an example of the case where the pattern images projected on the fundus are arbitrarily stored and the relationship between the pattern image and the corresponding peak position.
Figure 4B:
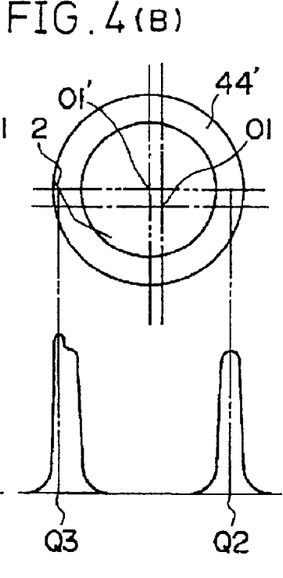
Figure 4C:
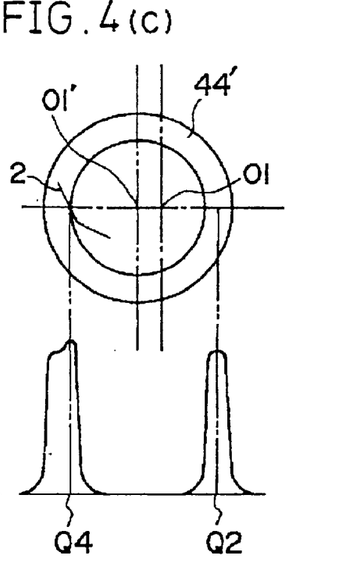
Figure 4D:
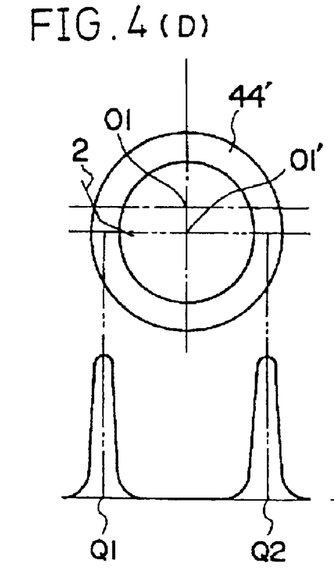
Figures 4E, 4F:
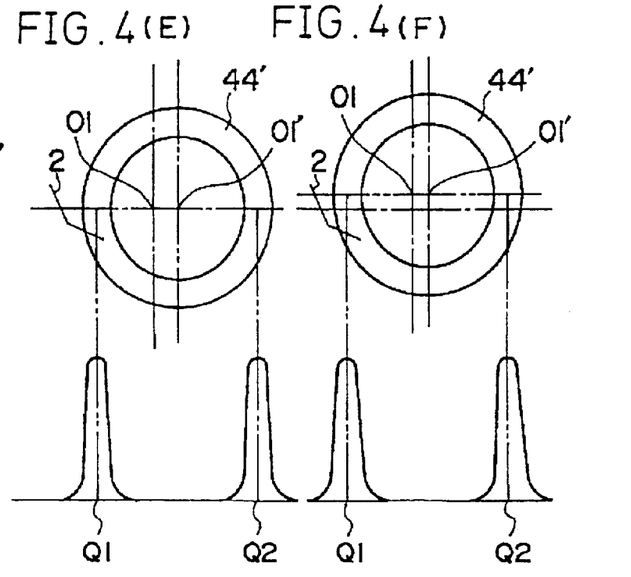

Thus, according to the embodiment of the present invention, a range on the orbital locus of the pattern image 44' which can be influenced by a scar 2 is an extremely small area as compared with a range which is not influenced. That is, in the case of the illustrated scar 2, the range that can be influenced is on the locus of the range shown in FIG. 4(B) or (C), and the other range can be regarded as being nearly the same as normal vision. Therefore, as the number of storages of the peak position onto a storage medium is increased, there is a high possibility that the fundus information about the portion which is not influenced by a scar 2 is fetched. Furthermore, by averaging the results of measurement of the distance between the centers of the width, there can be obtained results of measurement where reliability is high to the degree where a shift due to the presence of a scar 2 is negligible.

That is, the position on the fundus Er where a scar 2 exists depends on a subject to be tested. Therefore, when the pattern image 44' is projected merely at a shifted position (a deflected position), there is the possibility that a scar 2 will exist at the shifted position and there is the fear that a result of measurement will become a mistaken measurement. In the present invention, however, a pattern image is rotated and recorded plural times on a storage medium, and consequently, a possibility of fetching the pattern image 44" influenced by a scar 2 is reduced and a reliability in the result of measurement can be enhanced.

Although the pattern image 44' has been projected at a position shifted from the optical axis O1, there is no possibility that a reliability in measured data will be obstructed, because a constant relationship is maintained between the tested eye E and the main body of the apparatus by performing an alignment operation.

In the aforementioned embodiment, while the optical-axis deflection prism 49 has been inserted in a section shared by the; optical pattern-beam projection system 40 and the optical light-receiving system 50, the present invention is not limited to this. For example, if optical-axis deflection prisms of the same types are respectively arranged in the non-shared sections of the optical systems 40 and 50 so that the rotational angles of both optical-axis deflection prisms are always aligned with each other, similar operational effect will be obtained.

In the refractometer of the present invention, a mistaken measurement resulting from the vein or scar on a fundus can be prevented by providing a deflecting member on an optical path between the optical pattern-beam projection system and the optical light-receiving system for deflecting the optical axis.

Second Embodiment

Figure 6A:
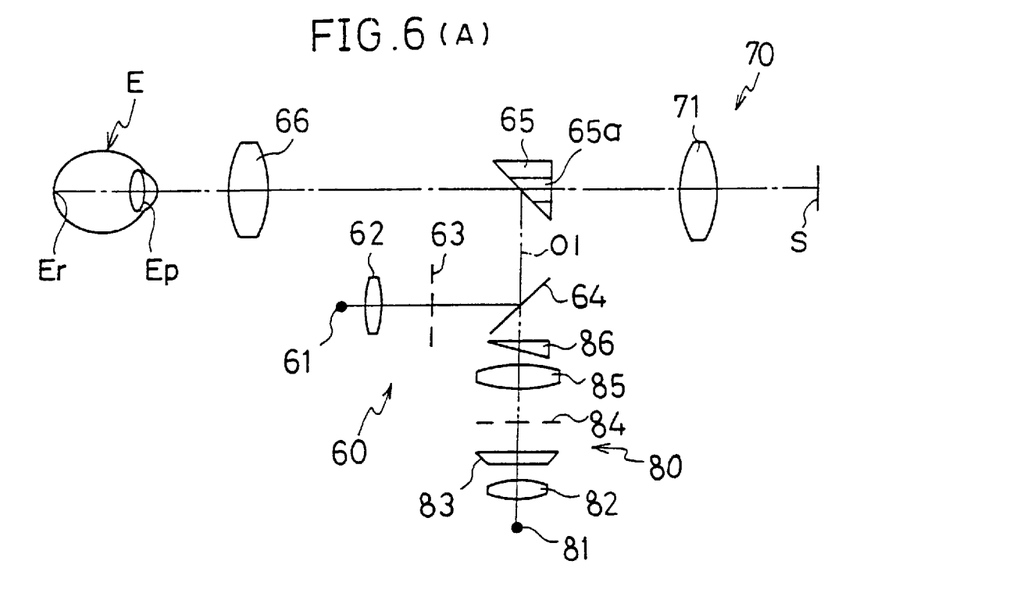
FIG. 6(A) is a schematic view showing a refractometer according to a second embodiment of the present invention.

FIG. 6A schematically illustrates the optical system of a refractometer according to a second embodiment of the present invention. In the figure, reference numeral 60 is an optical illumination-beam projection system which illuminates a fundus Er, reference numeral 70 is an optical light-receiving system which receives a reflected illumination light beam from the fundus Er to a light receiving element S, and reference numeral 80 is an optical pattern-beam projection system which projects a pattern light beam onto the fundus Er of a tested eye E to measure the refractive power of the tested eye E.

The optical illumination-beam projection system 60 is equipped with a halogen lamp 61, a collimator lens 62, a ring slit 63, a dichroic mirror 64, a holed prism 65, and an objective lens 66. The ring slit 63 and the pupil Ep of the tested eye E are conjugate with each other.

An illumination light beam emitted from the halogen lamp 61 is collimated by the collimator lens 62 and is transmitted through the ring slit 63. The transmitted light beam is reflected by the dichroic mirror 64 and the holed prism 65 and then is guided to the fundus Er via the objective lens 66.

The optical light-receiving system 70 has the aforementioned objective lens 66, the hole 65a of the aforementioned holed prism 66, an imaging lens 71, and a light receiving element S.

The illumination light beam reflected by the fundus Er is converged by the objective lens 66 and is transmitted through the hole 65a of the holed prism 65. The transmitted light beam is projected on the light receiving element S.

Figure 7:
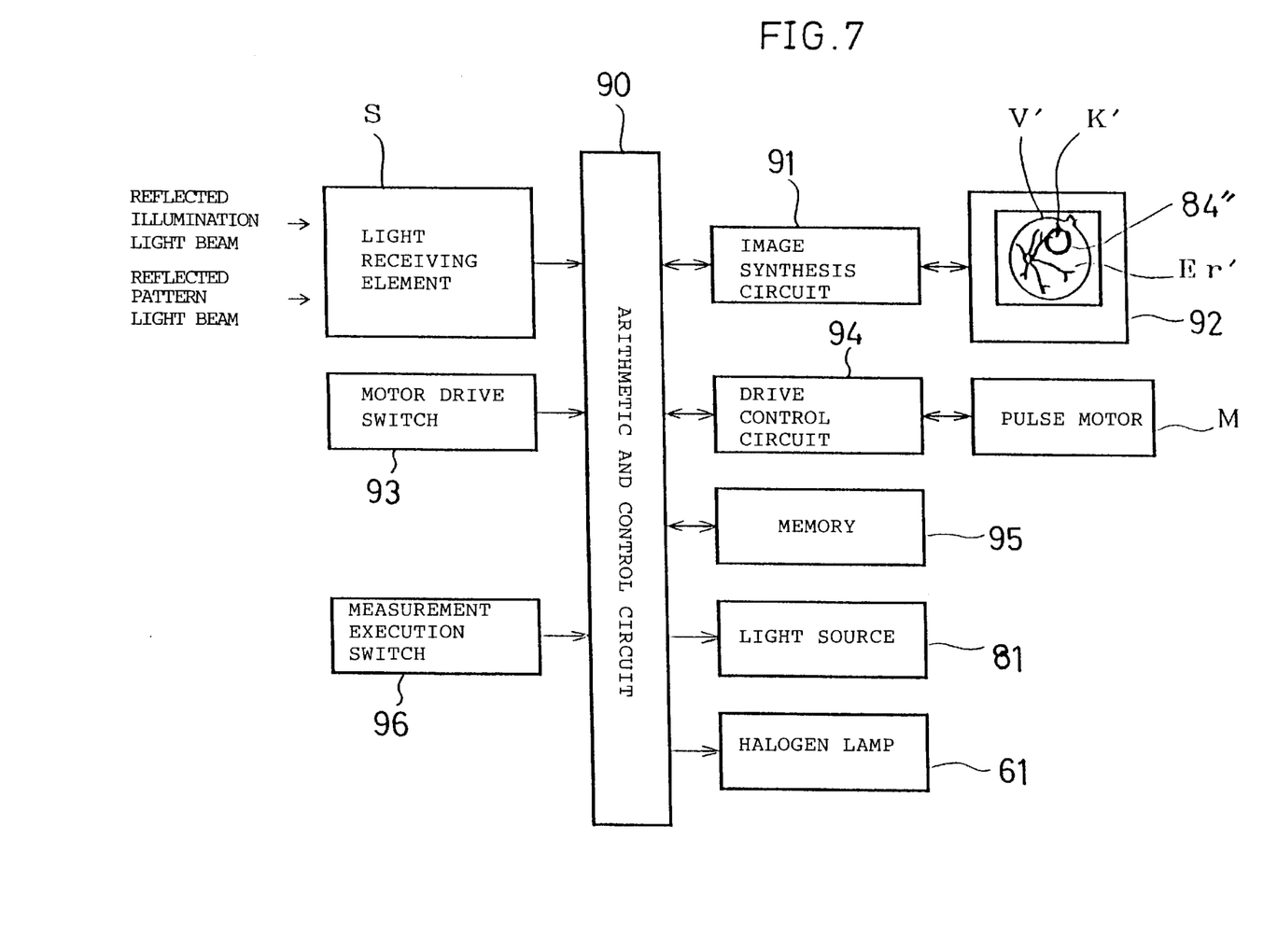
FIG. 7 is a block diagram showing the main control circuit of the refractometer according to the present invention.

The light receiving element S employs, for example, a two-dimensional CCD. As shown in FIG. 7, a fundus image Er' is displayed on a display means 92 via a computation control circuit 90 and an image synthesis circuit 91.

The optical pattern-beam projection system 80 is constituted by a light source 81, a collimator lens 82, a conical prism 83, a ring target plate 84, a relay lens 86, an optical-axis deflection prism 86 as an optical-axis deflecting member, the aforementioned dichroic mirror 64, the aforementioned prism 65, and the aforementioned objective lens 66. The ring target plate 84, the fundus Er, and the light receiving element S are arranged at mutually optical conjugate positions.

A light beam emitted from the light source 81 is collimated by the collimator lens 82 and is transmitted through the conical prism 83. The transmitted light beam is guided to the ring target plate 84. Next, the light beam is transmitted through a ring-shaped pattern portion formed in the ring target plate 84 and becomes a pattern light beam. The pattern light beam is transmitted through the relay lens 85. Next, in the state where the pattern light beam is deflected obliquely with respect to the principal axis O1 by the optical-axis deflection prism 86, the light beam is transmitted through the dichroic mirror 64. Thereafter, the deflected light beam reflected by the holed prism 65 is projected on the fundus Er by the objective lens 66.

Figure 8:
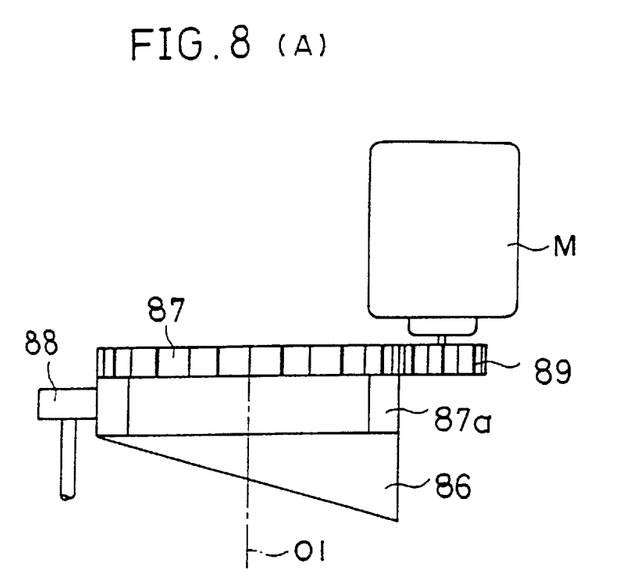
FIG. 8(A) is a side view showing an example of a mechanism for rotating the deflecting member.
FIG. 8(B) is a front view showing the mechanism of FIG. 8(A)

The optical-axis deflection prism 86, as shown in FIG. 8(A), is fixed to the bracket 87a of a ring-shaped driven gear 87. This ring-shaped driven gear 87 is supported by a plurality of rotatable support rollers 88 (three rollers for the case shown in FIG. 8(B)) and meshes with the drive gear 89 of a pulse motor M. In FIG. 8(B), reference numeral 80' denotes the optical path (effective range) of the optical pattern-beam projection system 80 formed by the configuration of the aperture of the ring-shaped driven gear 87.

The pulse motor M, as shown in FIG. 7, is driven in interlock with the operation of a motor drive switch 93, and the optical-axis deflection prism 86 is rotated on the basic optical axis O1 by this pulse motor M.

Figure 6B:
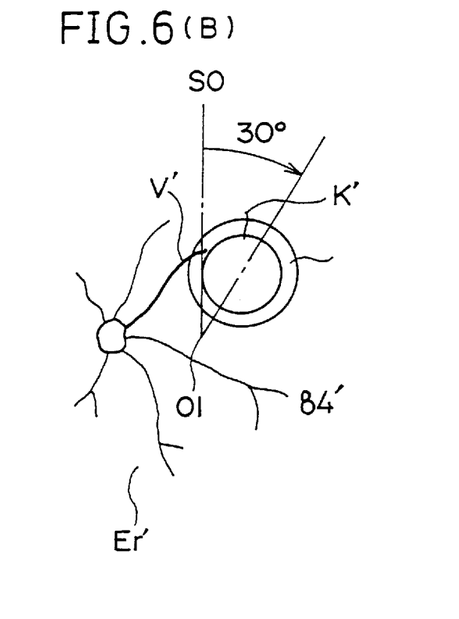
FIG. 6(B) is an explanatory diagram of the state where a pattern image overlaps a vein and a scar on the fundus.

For example, if an angle of 30 degrees is set by using the motor drive switch 93 as a ten-key pad, the optical-axis deflection prism will be rotated on the base axis O1 by 30 degrees. As shown in FIG. 6(B), the image 84' of a pattern light beam that is projected onto the fundus Er (which will hereinafter be referred to as a pattern image 84') is projected in an eccentric state having base axis O1 as its center and at a position shifted from reference position S0 by 30 degrees.

Also, when an angle of 60 degrees is set with the ten-key pad, a pattern image 84' that is projected on the fundus Er is likewise projected in an eccentric state having base axis O1 as its center and at a position shifted from reference, position S0 by 60 degrees. That is, if the ten-key pad is employed as a means of setting a drive quantity for the pulse motor M, a projected position of a pattern image on the fundus Er can be suitably changed from the base position S0.

An actual projected position of the pattern image 84' on the fundus Er by rotation of the optical-axis deflection prism 86 is obtained with the computation control circuit 90, before a pattern light beam is actually projected onto the fundus Ef, by detecting the drive quantity of the pulse motor M as a pulse signal with the drive control circuit 94. Also, the result of detection is stored in a memory 95. Note that the eccentric angle may also be set to a constant space (for example, a space of ±5°), and the projected positions of the pattern image may previously be stored and set at intervals of the constant eccentric angle.

On the other hand, based on the detection result of the computation control circuit 90, the projected position of the pattern light beam on the fundus Er is detected in correspondence with rotation of the optical-axis deflection prism 86, a temporary pattern image 84" based on the detection result of the projected position of the pattern beam is synthesized to the fundus image Er' by the image synthesis circuit 91 and is displayed on the display means 92.

The oculist confirms whether a scar K exists on the fundus Er, based on the fundus image Er' displayed on the display means 92. Also, before lighting the light source 81 by operation of a measurement execution switch 96 and actually measuring the refractive power of an eye, it is confirmed whether a scar K or vein V exists at a position on the fundus Er where the pattern image 84' will be projected, by the positional relationship between the fundus image Er', the scar image K', and vein image V', displayed on the display means 92, and the temporary pattern image 84".

If neither a scar K nor a vein K exists at the displayed position of the temporary pattern image 84", the measurement execution switch 96 will be operated and the halogen lamp 61 will be turned off. At the same time, a light beam is emitted from the light source 81 and the pattern image 84' is projected onto the fundus Er. The reflected pattern light beam of this pattern image 84' is projected on the light receiving element S through the optical light-receiving system 70. Based on the positional information about the peal value of the reflected pattern beam projected on this light receiving element S, the inter center distance of the width is computed and therefore the refractive power of the tested eye can be measured. Since the measuring method is well known in the prior art, a description thereof is omitted.

Figure 6C:
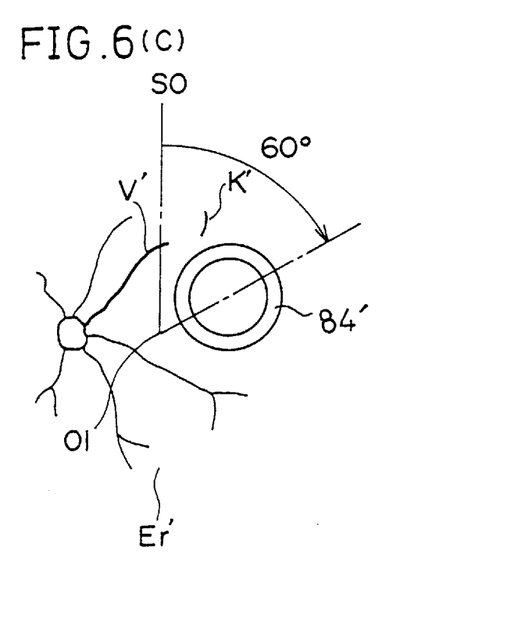
FIG. 6(C) is an explanatory diagram of the state where a pattern image is moved so as not to overlap a vein and a scar on the fundus.

Thus, in the present invention, the pattern light beam for measurement is not projected at a position which overlaps the scar K and veins V on the fundus Er, by confirming the projected position of the pattern image 84' with the fundus image Er and the pattern image 84" displayed on the display means 92. Consequently, a possibility of fetching the pattern image 84' influenced by the scar K and veins V on the fundus is reduced and a reliability in the result of measurement can be enhanced.

While the pattern image 84' has been projected at a position shifted from the optical axis O1, there is no possibility that a reliability in measured data will be obstructed, because a constant relationship is maintained between the tested eye E and the main body of the apparatus by performing an alignment operation.

Also, in the aforementioned embodiment, the optical-axis deflection prism 86 has been driven by the pulse motor M, and also a position at which the pattern image 84' is projected has been detected based on a pulse signal which is output according to the driving of the optical-axis deflection prism 86. However, the present invention is not limited to this. For example, it is also possible to drive the optical-axis deflection prism 86 by a dial type rotation control mechanism and to detect the projected position of the pattern image 84' by detecting the drive quantity with a rotary encoder. In addition, the optical-axis deflection prism 86 may be detachable from the optical path of the optical pattern-beam projection system 80. Furthermore, a rotary prism with two prisms rotatable independently of and in synchronization with each other may also be employed as an optical-axis deflecting member in order to deflect an optical axis by rotating either prism on the base axis O1. Moreover, the projected position of the pattern image 84' on the fundus can be deflected by shifting the light source within a plane perpendicular to the base axis O1.

What is claimed is:

1. A refractometer comprising:

an optical pattern-beam projection system for projecting a pattern light beam onto a fundus of an eye of a subject to measure refractive power of said eye;

an optical light-receiving system for receiving said pattern light beam reflected at said fundus to compute the refractive power of said eye; and a deflecting member inserted in an optical path of said optical pattern-beam projection system for deflecting said pattern light beam with respect to an optical axis of said optical pattern-beam projection system and then projecting the deflected pattern light beam onto said fundus.

2. The refractometer as set forth in claim 1, wherein said optical pattern-beam projection system and said optical light-receiving system share a portion of an optical system and wherein said deflecting member is inserted into the shared portion.

3. The refractometer as set forth in claim 2, further comprising a driving means for rotating said deflecting member about said optical axis of said optical pattern-beam projection system.

4. The refractometer as set forth in claim 1, further comprising:

an optical illumination system for illuminating said fundus;

an optical observation system for observing an image on said fundus illuminated by said optical illumination system; and setting means for setting a drive quantity which is driven by driving means.

5. The refractometer as set forth in claim 4, further comprising:

position detection means for detecting a position of said deflecting member;

computation means for computing a position on the fundus of said eye where said pattern light beam is projected, based on a detection result of said position detection means; and display means for synthesizing and displaying said image on said fundus and said pattern image, based on a computation result of said computation means.

6. A refractometer comprising:

an optical pattern-beam projection system for projecting a pattern light bear onto a fundus of an eye of a subject to measure refractive power of said eye;

an optical light-receiving system for receiving said pattern light beam reflected at said fundus to compute the refractive power of said eye;

a first deflecting member provided in an optical path of said optical pattern-beam projection system for deflecting said pattern light beam with respect to an optical axis of said optical pattern-beam projection system and then projecting the deflected pattern light beam onto said fundus; and a second deflecting member provided in an optical path of said optical light-receiving system for deflecting said pattern light beam reflected at said fundus toward an optical axis of said optical light-receiving system.

7. The refractometer as set forth in claim 6, wherein said deflecting members are inserted at positions which are approximately conjugate with a pupil of said eye.

8. The refractometer as set forth in claim 7, wherein said deflecting members are rotatable about the optical axes in synchronization.

* * * * *